(12) United States Patent
Reiter et al.

(10) Patent No.: US 9,839,737 B2
(45) Date of Patent: Dec. 12, 2017

(54) TUBING SET HAVING A GATE FOR THE CONNECTION OF VIALS

(75) Inventors: Reinhold Reiter, Crema (IT); Massimo Fini, Mirandola (IT); Alain Veneroni, Spino d'Adda (IT); Johannes Bartholomaeus, Aachen (DE); Gerhard Wiesen, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 631 days.

(21) Appl. No.: 13/505,320

(22) PCT Filed: Oct. 25, 2010

(86) PCT No.: PCT/EP2010/066056
§ 371 (c)(1),
(2), (4) Date: Jul. 12, 2012

(87) PCT Pub. No.: WO2011/054693
PCT Pub. Date: May 12, 2011

(65) Prior Publication Data
US 2012/0271274 A1 Oct. 25, 2012

(30) Foreign Application Priority Data
Nov. 4, 2009 (EP) .................................. 09175001

(51) Int. Cl.
*A61M 1/36* (2006.01)

(52) U.S. Cl.
CPC ........ *A61M 1/3672* (2013.01); *A61M 1/3621* (2013.01); *A61M 1/3627* (2013.01); *A61M 2205/07* (2013.01); *A61M 2205/3331* (2013.01)

(58) Field of Classification Search
CPC .......... A61M 5/365; A61M 1/14; A61M 1/36; A61M 1/34; A61M 1/3621; A61M 1/3627; A61M 1/3672; A61M 2205/07; A61M 2205/3331
See application file for complete search history.

(56) References Cited

U.S. PATENT DOCUMENTS

| | | |
|---|---|---|
| 4,396,016 A | 8/1983 | Becker |
| 5,897,526 A | 4/1999 | Vaillancourt |
| 7,572,489 B2 | 8/2009 | Dröschel et al. |

(Continued)

FOREIGN PATENT DOCUMENTS

| | | |
|---|---|---|
| EP | 0 192 588 | 8/1986 |
| EP | 0 568 265 | 11/1993 |

(Continued)

*Primary Examiner* — Imani Hayman
(74) *Attorney, Agent, or Firm* — Jacobson Holman, PLLC.

(57) ABSTRACT

A tubing set suitable for use in co-operation with a hemodialysis machine includes an out-tube for supplying the blood from the patient to a filter of the machine, an in-tube for supplying the blood from the filter back to the patient, a drip chamber placed along one of the tubes, adapted to let the blood drip through an air buffer, and a vial gate for the connection of vials containing drugs to be delivered into the blood. The vial gate includes a delivery lumen, suitable for delivering the drug from the vial to the drip chamber, and a vent lumen, suitable for providing air inside the vial in order to replace the delivered drug.

17 Claims, 7 Drawing Sheets

(56) References Cited

U.S. PATENT DOCUMENTS

2002/0115981 A1    8/2002  Wessman
2003/0229330 A1*  12/2003  Hickle .................. A61M 5/142
                                                    604/411
2011/0004143 A1*   1/2011  Beiriger et al. ............. 604/6.11

FOREIGN PATENT DOCUMENTS

| EP | 0 904 789 | 3/1999 |
| JP | 11-227845 | 8/1999 |
| JP | 2002-248166 | 9/2002 |
| WO | WO 87/07159 | 12/1987 |
| WO | WO 2010/100074 | 9/2010 |

* cited by examiner

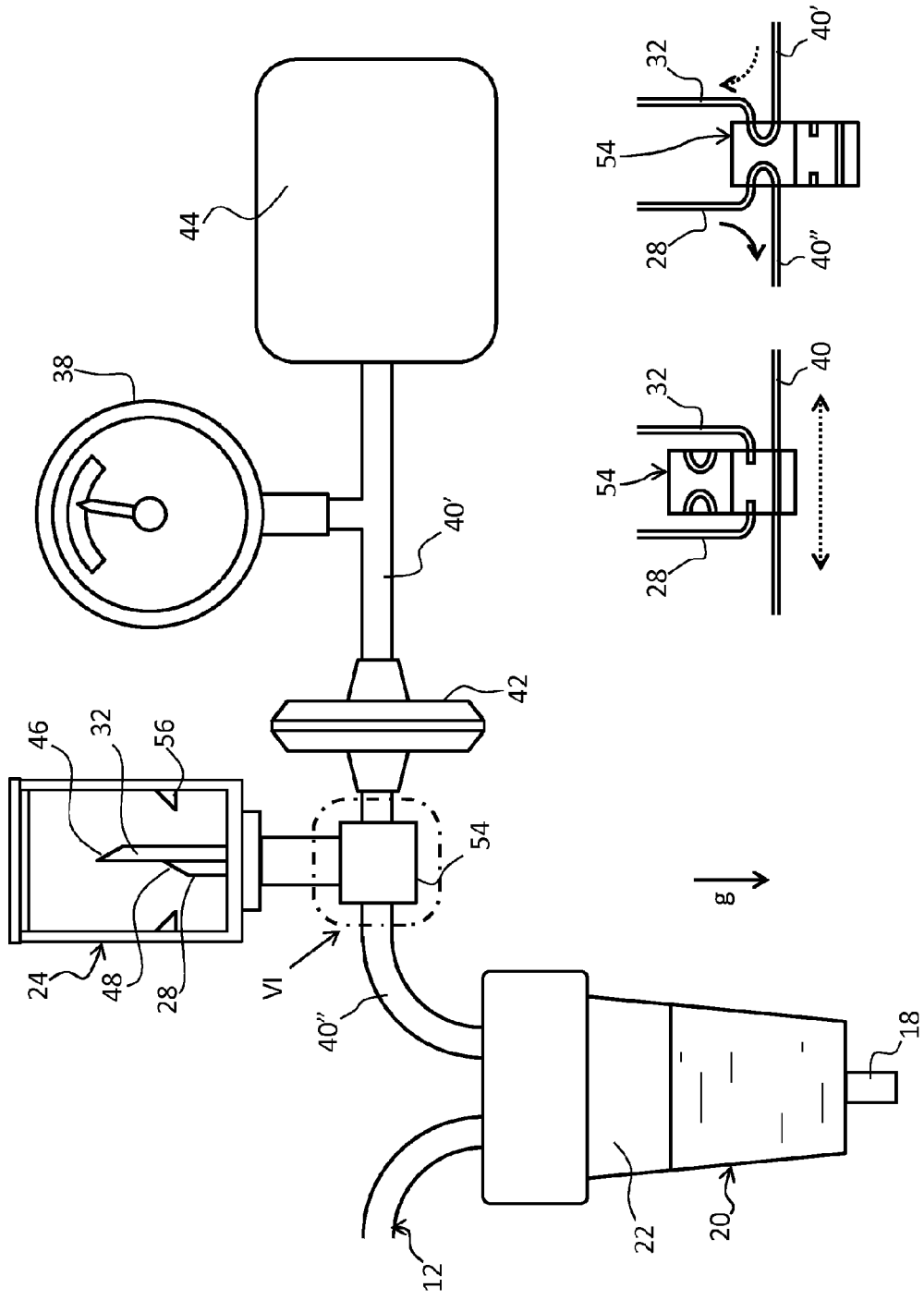

TUBING SET HAVING A GATE FOR THE CONNECTION OF VIALS

CROSS-REFERENCE TO RELATED APPLICATIONS

This is a national stage of PCT/EP10/066056 filed Oct. 25, 2010 and published in English, which claims the priority of European number 09175001.8 filed Nov. 4, 2009, hereby incorporated by reference.

BACKGROUND OF THE INVENTION

1. Field of Invention

DESCRIPTION

The invention concerns a tubing set for an extracorporeal circuit comprising a gate for the connection of vials containing drugs, in particular a tubing set intended to be used with hemodialysis machines. The invention further concerns a method for delivering drugs by means of the tubing set.

2. Description of the Prior Art

In hemodialysis treatments which require an extracorporeal circulation it is often necessary to administer different drugs or therapeutic substances to the patient. The presence of the tubing set advantageously makes it possible to avoid the administering of the drug taking place through puncture carried out directly on the patient himself.

During the hemodialysis treatments it often becomes necessary to administer different drugs or therapeutic substances, like for example iron, heparin, erythropoietin, vitamins and antibiotics. The infusion of such substances in the extracorporeal circuit is currently carried out through conventional syringes. The substance is drawn from the vial in which it is supplied by the producer and is then injected into a special puncturable cap provided along the tubing set. Thus there is a double transfer of the substance: firstly from the vial to the syringe and then from the syringe to the circuit.

Such an operation therefore requires the use of disposable materials, such as the syringe and the respective needle, just to transfer the substance from the vial to the tubing set. Moreover, the use of needles always carries the risk of the service staff being pricked.

Finally, some of the quoted substances need to be administered slowly, over a few minutes. From this it can easily be understood how the administering of various substances to more than one patient represents a considerable workload for the nursing staff responsible for the treatment.

WO 87/07159 discloses a medical fluid administration set which is intended for infusions related to an intravenous therapy; such set is not suitable for use in co-operation with a hemodialysis machine.

SUMMARY OF THE INVENTION

The aim and the tasks indicated above are accomplished by a tubing set and by a method as described herein.

A task of the present invention is to avoid the double transfer of the substance.

Another task of the present invention is to make it possible to avoid the use of conventional syringes and the respective needles.

Another task of the present invention is to allow automated processes for the delivery of any medicament, e.g. to allow slow administering of the substances that require it without needing the active presence of the service staff to do so.

The aim and the tasks indicated above are accomplished by a tubing set according to claim 1 and by a method according to claim 13.

BRIEF DESCRIPTION OF THE DRAWINGS

The characteristics and the further advantages of the invention shall become clear from the following description of some embodiments, given for indicating and not limiting purposes with reference to the attached drawings, in which:

FIG. 5 schematically represents the detail indicated with V in FIG. 2;

FIGS. 6.a and 6.b schematically represent the detail indicated with VI in FIG. 5 in two different configuration;

DETAILED DESCRIPTION OF THE PREFERRED EMBODIMENTS

Figure 1:
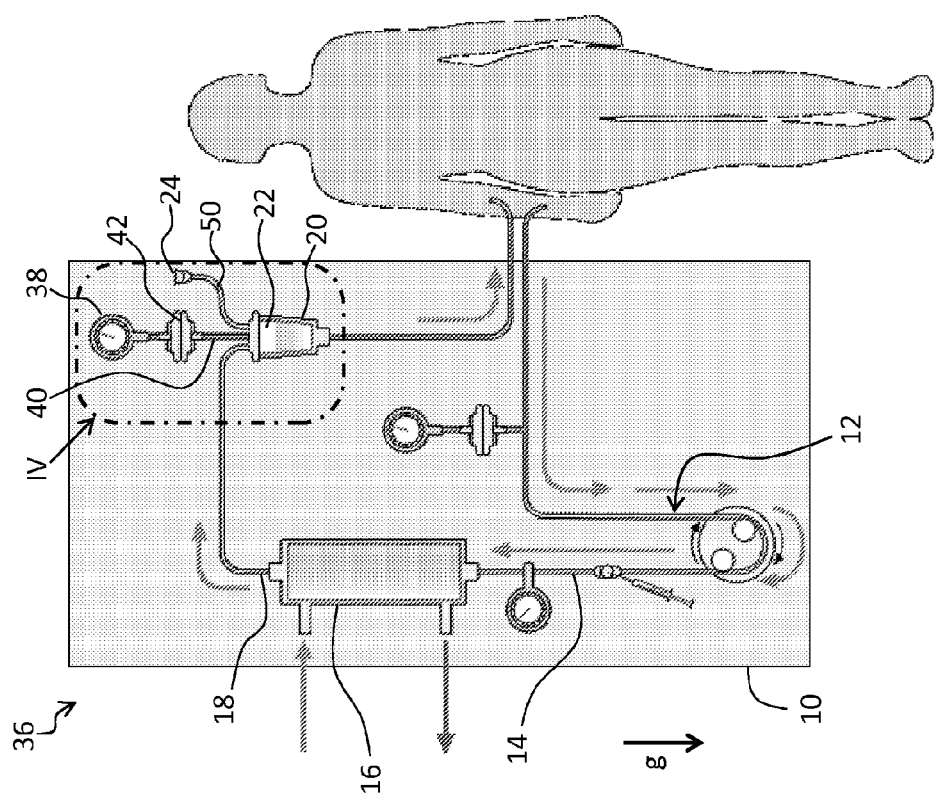
FIG. 1 schematically represents a first extracorporeal circuit used in a hemodialysis treatment according to the invention.

Further scope of applicability of the present invention will become apparent from detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

With specific reference to the enclosed figures, the reference 10 indicates a hemodialysis machine where a patient's blood is passed through a filter to remove waste products. The machine 10, known per se, is provided with a disposable tubing set 12 which comprises:
- an out-tube 14 for supplying the blood from the patient to a filter 16 of said machine 10;
- an in-tube 18 for supplying the blood from the filter 16 back to the patient;
- a drip chamber 20 placed along one of said in-tube 18 or out-tube 14, adapted to let the blood drip through an air buffer 22; and
- a vial gate 24 for the connection of vials 26 containing drugs to be delivered into the blood.

The vial gate 24 according to the invention comprises a delivery lumen 28, suitable for delivering the drug 30 from the vial 26 to the drip chamber 20, and a vent lumen 32, suitable for providing air 34 inside the vial 26 in order to replace the delivered drug.

In the description of the invention, reference will be made to the spatial arrangement of the extra-corporeal circuit 36 which ensures correct operation thereof. During operation of the invention, in fact, the force of gravity plays a decisive part, especially in the embodiments according to FIGS. 1, 3, 4 and 7-11. In particular, it will be assumed below that the force of gravity is directed as shown by the vector g in the enclosed figures (side views). The vector g therefore defines the vertical direction and is oriented from the top downwards.

Reference is made to air 34 to be provided inside the vial 26 in order to replace the delivered drug. In the present description, the term "air" is to be broadly interpreted, i.e. it can be referred to actual air or to another physiologically acceptable gas or gas mixture, for example nitrogen (N).

According to some embodiment of the invention, the vent lumen 32 is suitable to put in fluid communication the interior of the vial 26 with a closed air reservoir which is fluidly separated from outer environment. Preferably, such air reservoir is maintained under a pressure which is different from atmospheric pressure. More preferably, the air reservoir pressure is controlled on the basis of the pressure in the air buffer 22 of said drip chamber 20. In the following description, some examples of such air reservoir will be given with reference to specific embodiments of the tubing set 12 according to the invention.

According to some embodiment of the invention, the vial gate 24 comprises means 56 for ensuring a safe connection of the vial 26. Such means, which are not shown in detail in the attached figures, are preferably designed to ensure a tight closure of the extra-corporeal circuit 36 in absence of any vial 26. Moreover, the safe connection means 56 are preferably so arranged that the fluid connection can be opened only when a vial 26 is properly placed on the vial gate 24 and, respectively, the vial 26 can be removed only when the fluid connection is closed.

Some safe connection means 56 suitable for such use are known in the art. Italian Patent Application number 102009A000455 in the name of Borla Industrie S.p.A. discloses a device which, among some other technical features, comprises safe connection means which are suitable for the present use.

According to some embodiments of the invention, the vial gate 24 further comprises means 58 for adjusting the delivery rate of the drug 30. The adjusting means 58 are well known in the art. They can comprise for example an adjustable clamp suitable for adjustably obstructing the inner cross section of the delivery lumen 28.

Figure 2:
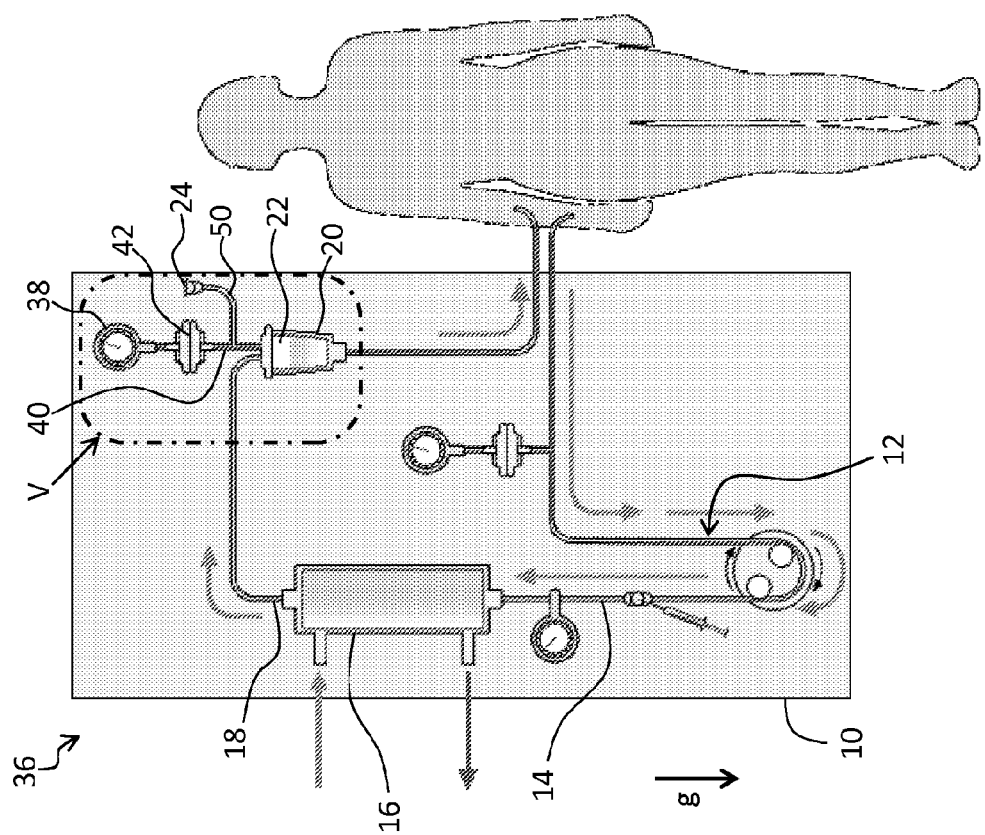
FIG. 2 schematically represents a second extracorporeal circuit used in a hemodialysis treatment according to the invention.
Figure 3:
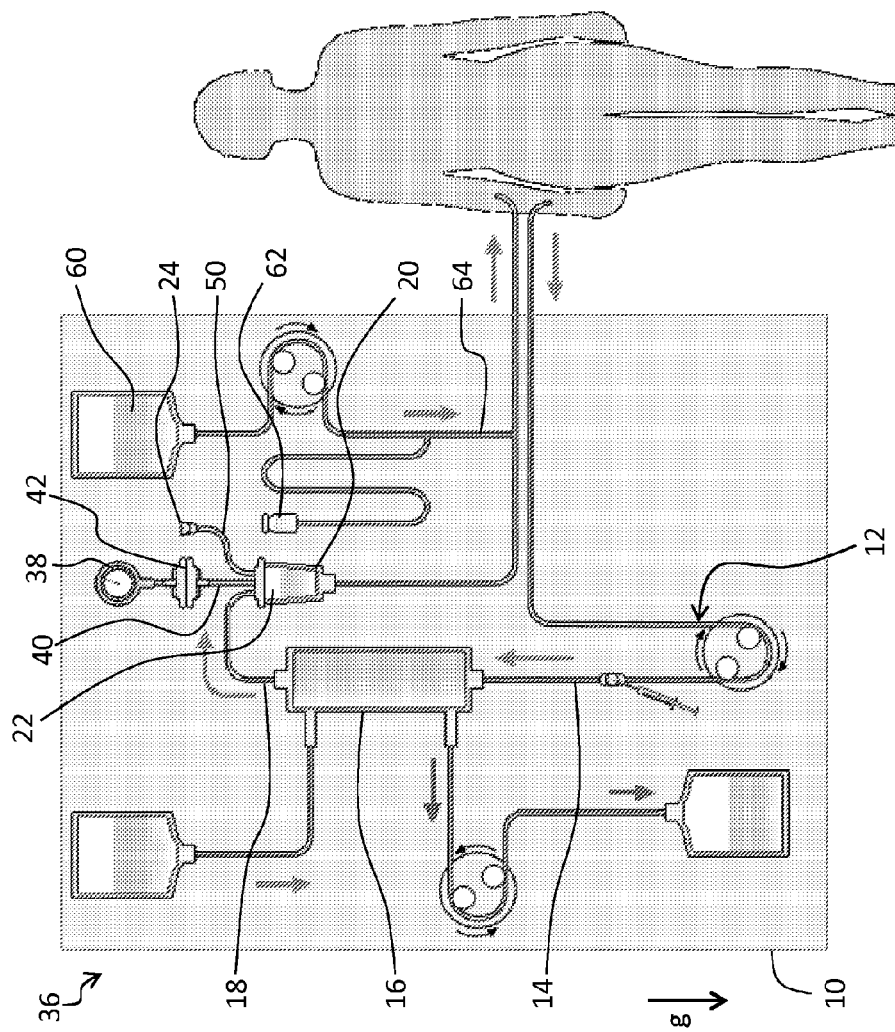
FIG. 3 schematically represents a third extracorporeal circuit used in a hemodialysis treatment according to the invention.

With reference to FIGS. 1 to 3, an extra-corporeal circuit 36 is described which comprises a tubing set 12 according to the invention and which is associated with a hemodialysis machine 10 known per se.

The tubing set 12 mainly comprises an out-tube 14 and an in-tube 18. Along one of said tubes at least a drip chamber 20 is provided in order to remove from the blood any possible gas bubble. In the enclosed figures and in the following description, the drip chamber 20 is considered to be placed along the in-tube 18 which supplies the filtered blood back to the patient. The drip chamber 20 is preferably placed along the in-tube 18, thus avoiding the drug 30 to pass through the filter 16, by which it could be easily removed and disposed of together with the waste products. However, nothing would substantially change by placing the drip chamber 20 along the out-tube or another auxiliary tube of the circuit 36.

The drip chamber 20 provides an air buffer 22 for receiving and stopping any possible gas bubble contained in the blood. The air buffer 22 is also connected to a pressure transducer 38 by means of a proper pressure conduit 40. Such pressure transducer 38 is intended to constantly provide a measurement of the pressure inside the drip chamber 20. The pressure transducer 38 is protected by a transducer protector 42 placed along the conduit 40. The transducer protector 42 comprises a hydrophobic semi-permeable membrane which is gas-permeable and liquid-tight. This arrangement, known per se, is intended to avoid any possible blood contamination of the non-disposable portion of the extra-corporeal circuit 36. At the same time it allows the air to freely and safely move along the conduit 40 (dotted arrow on FIG. 6.*a*) so as to instantly provide the pressure value from the drip chamber 20 to the pressure transducer 38.

Figure 4:
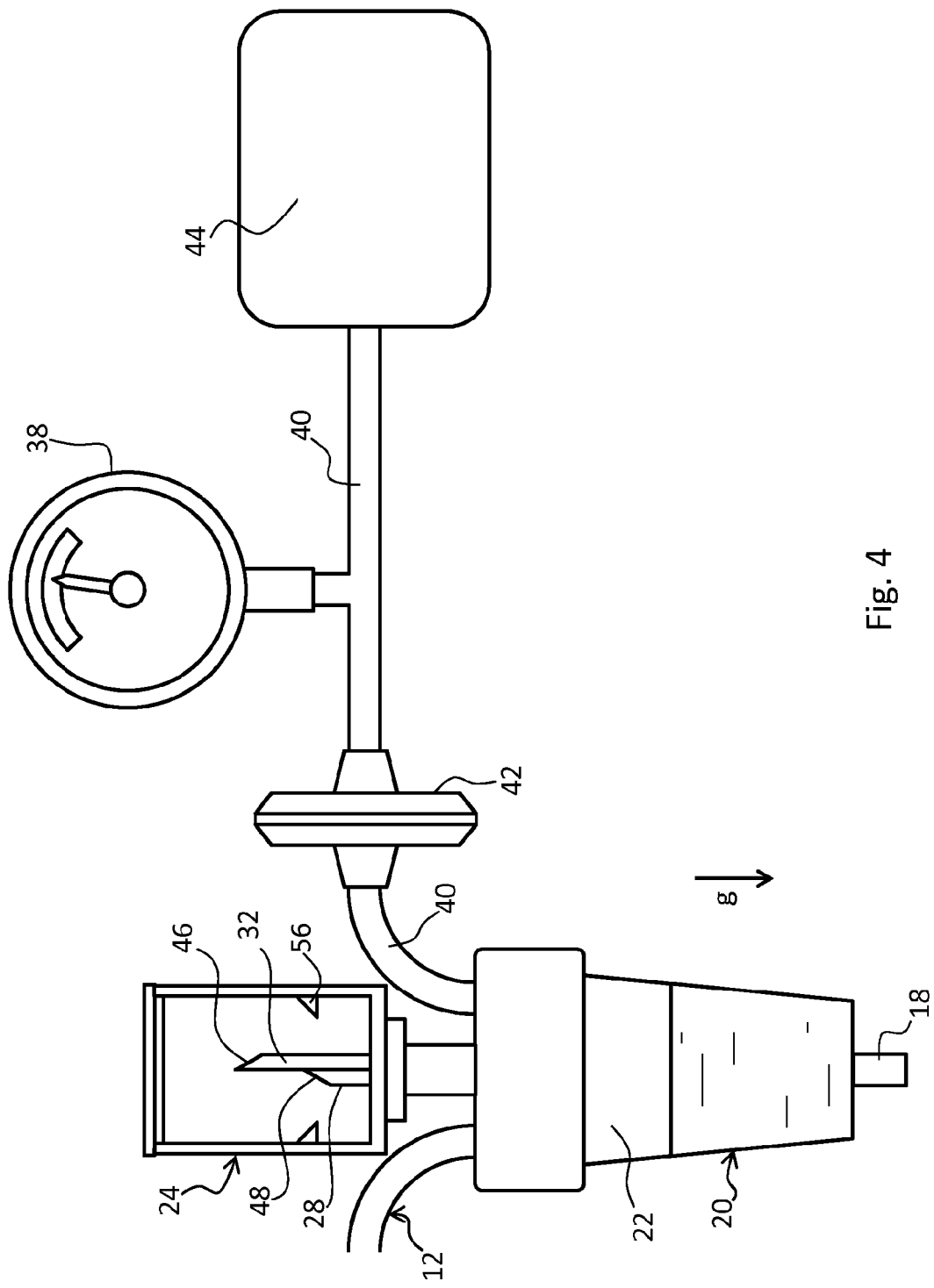
FIG. 4 schematically represents the detail indicated with IV in FIG. 1.
Figure 7:
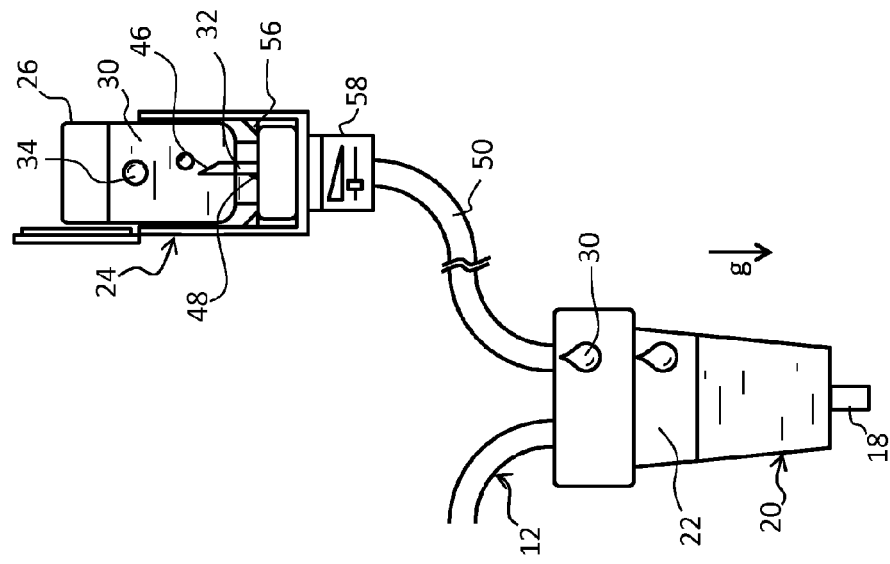
FIG. 7 schematically represents a vial and a vial gate according to the invention.

The proper operation of the pressure transducer 38 and the safe removal of the gas bubbles from the blood flow strictly depend on the presence of the air buffer 22 inside the drip chamber 20. Since the air buffer 22 is crucial, an air pump 44 is provided on the machine 10 to restore the correct air amount in the drip chamber 20, if needed. An air pump 44 is schematically shown in FIGS. 4 and 5. In practice, in a manner known per se, if the blood level becomes too high (i.e. the air buffer 22 is reduced), the service staff or the dialysis machine 10 itself operates the pump 44 to supply air in the drip chamber so as to restore the correct blood level.

A first type of embodiments of the invention will be now disclosed in detail, with specific reference to FIGS. 1, 3, 4 and 7-11. In such embodiments, the vial gate 24 is designed to take advantage of gravity for the delivery of the drug 30. In the following, such type of embodiments will be referred to as gravity-driven vial gates.

According to such embodiments, the vial gate is directly connected to the drip chamber 20. In particular, the vent lumen 32 puts in communication the interior of the vial 26 with the air buffer 22 (embodying the air reservoir described above); the delivery lumen 28 puts in communication the interior of the vial 26 with the drip chamber 20.

Accordingly, the drug 30 is drawn down along the delivery lumen 28 by gravity while air 34 goes up along the vent lumen 32. The volume of the delivered drug 30 is thus automatically compensated by an equal volume of air 34, accordingly the pressure inside the vial 26 is promptly equalized to the pressure inside the drip chamber 20.

Figure 11:
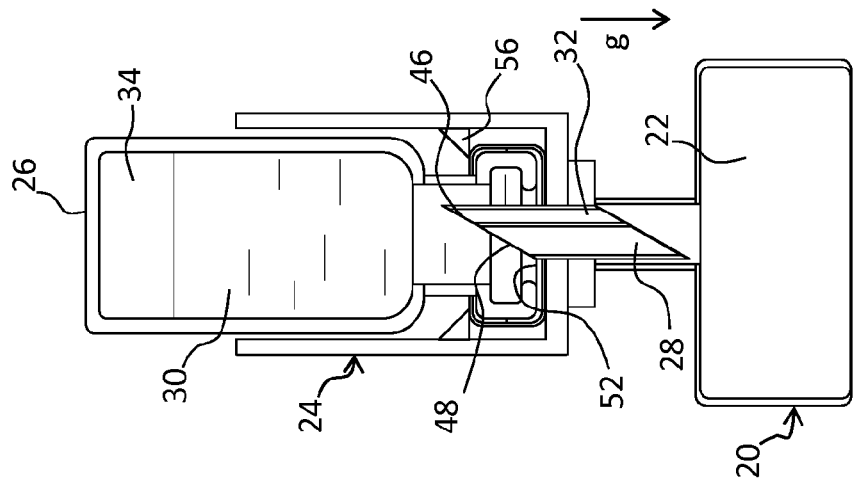
FIGS. 9 to 11 represent cross sections of assemblies similar to the one of FIG. 8.
Figure 10:
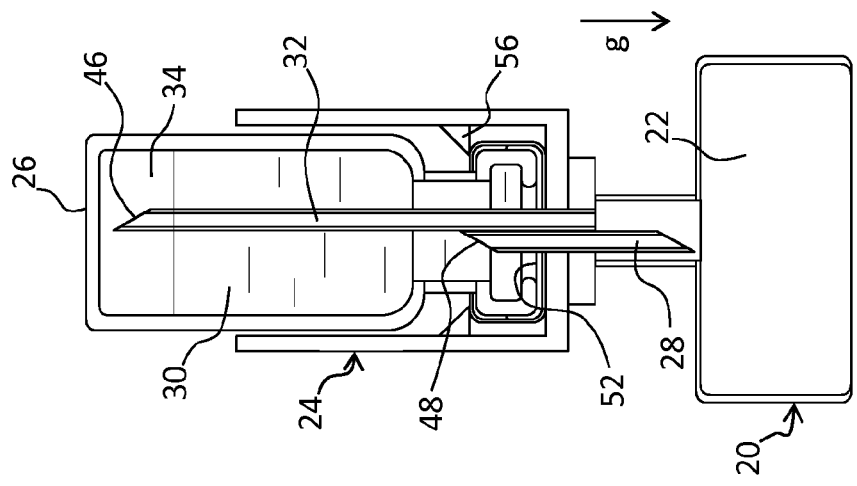
Figure 9:
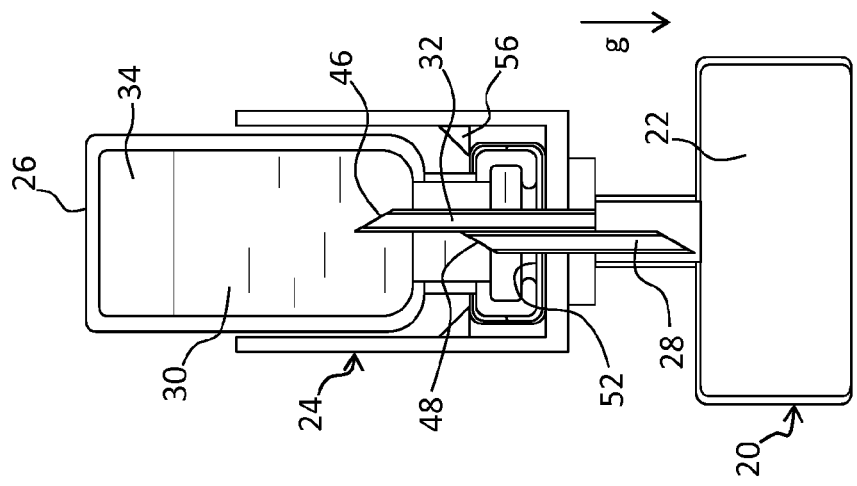

According to such embodiments, the top portion of the delivery lumen 28 is quite different from the top portion of the vent lumen 32. The difference between the two top portions, both of which have to be introduced inside the vial 26, are intended to facilitate the drug 30 to flow downward into the delivery lumen 28 rather than into the vent lumen 32. Thus at the same time air 34 is allowed to flow upward along the vent lumen 32, without any conflict occurring with the downflowing drug 30. Reference is made in the following to FIGS. 9 to 11, where both the top portions of the delivery lumen 28 and of the vent lumen 32 comprise a hollow needle.

The top end 46 of the vent lumen 32 can advantageously reach a higher position inside the vial 26 with respect to the top end 48 of the delivery lumen 28. In particular, according to the embodiment of FIG. 10, the top end 46 of the vent lumen 32 is configured to reach the air bubble contained inside the top of the upside-down vial 26. According to such embodiment, the delivery of the drug 30 involve the air 34 to be sucked directly from the air buffer 22 in the drip chamber 20 into the air bubble in the top of the vial 26.

According to other embodiments (e.g. those of FIGS. 8, 9 and 11) the top end 46 of the vent lumen 32 is only slightly higher than the top end 48 of the delivery lumen 28, such that both of them are submerged by the liquid drug 30 at the connection of the full vial 26 on the vial gate 24. The different height inside the vial 26 involve different pressures for the liquid drug 30 surrounding the top ends 46 and 48 of the two lumina. In particular, the higher pressure acting on the lower portion of the liquid drug 30 facilitates the priming of the delivery lumen 28 instead of the vent lumen 32.

Figure 8:
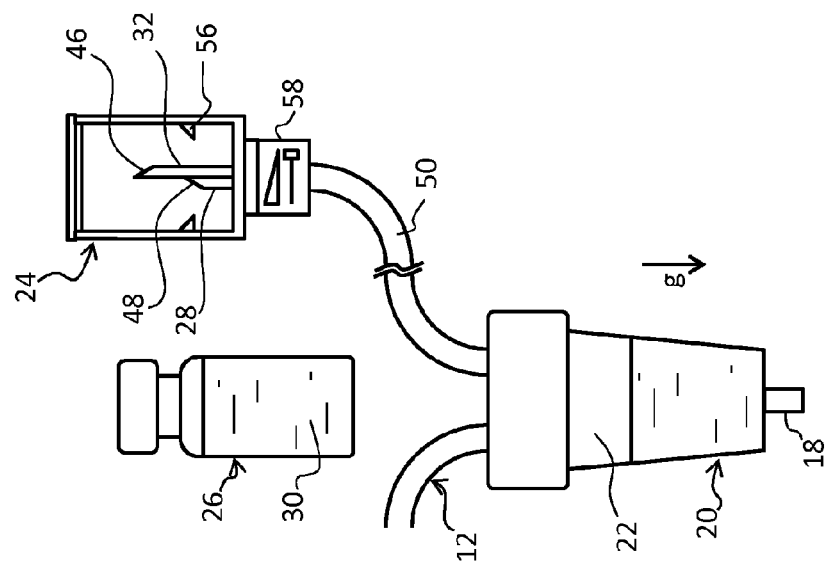
FIG. 8 schematically represents the vial connected on the vial gate of FIG. 7.

According to the above embodiments, the delivery of the drug 30 involve the air 34 to be sucked from the air buffer 22 of the drip chamber 20 into the liquid drug 30 so as to form bubbles which rise up to the top of the vial 26 (see also FIG. 8).

According to other embodiments (e.g. that of FIG. 11), the inner diameter of the top end 48 of the delivery lumen 28 is larger than the inner diameter of the top end 46 of the vent lumen 32. Facing the different diameters of the two top ends 46 and 48, the liquid drug 30, due to its surface tension, enters much more easily the larger one. Thus such arrangement facilitates the priming of the delivery lumen 28 instead of the vent lumen 32.

In all the gravity-driven embodiments, in their proper use configuration, the vial gate 24 is preferably located above the drip chamber 20. According to some embodiments (e.g. those shown in FIGS. 4 and 9-11) the vial gate 24 is directly mounted on the top wall of the drip chamber 20. According to some other embodiments (e.g. that shown in FIGS. 7 and 8) the vial gate 24 is mounted in a remote position with respect to the drip chamber 20 and is connected thereto by means of a double tube 50. Any of such different configurations may be advantageously adopted in order to deal with specific issues deriving from the overall arrangement of the dialysis machine 10.

A second type of embodiments of the invention will be now disclosed in detail, with specific reference to FIGS. 2, 5 and 6. In such embodiments, the vial gate 24 is designed to take advantage of an air pump 44 for the delivery of the drug 30. In the following, such type of embodiments will be referred to as air-driven vial gates.

According to a first type of air-driven embodiments of the invention, the air-pump 44 is the one already comprised in the machine 10 for controlling the air buffer 22 inside the drip chamber 20. According to such air-driven embodiments, the vial gate 24 is placed along the pressure conduit 40, between the drip chamber 20 and the transducer protector 42. In particular, the vent lumen 32 puts in communication the interior of the vial 26 with the branch 40' of the pressure conduit 40 which comes from the air pump 44 through the transducer protector 42 (the branch 40' embodying the air reservoir described above); the delivery lumen 28 puts in communication the interior of the vial 26 with the branch 40" of the pressure conduit 40 which goes to the drip chamber 20.

According to a second type of air-driven embodiments of the invention, the air-pump 44 is not the one for controlling the air buffer comprised in the machine 10, but is an additional air pump specifically provided for delivering the drug 30. This additional air pump may also be comprised in the machine or may be a separate device. Similarly to the first type of air-driven embodiments disclosed above, the vial gate 24 is placed along a pressure conduit 40, between the drip chamber 20 and the air pump 44. In particular, the vent lumen 32 puts in communication the interior of the vial with the branch 40' of the pressure conduit 40 which comes from the air pump 44 (the branch 40' embodying the air reservoir described above); the delivery lumen 28 puts in communication the interior of the vial 26 with the branch 40" of the pressure conduit 40 which goes to the drip chamber 20. Preferably, between the air pump 44 and the vial gate 24, a pressure transducer 38 and a transducer protector 42 are provided.

According to all the air-driven embodiments, when the air pump 44 introduces a volume of air inside the vial 26, the increased pressure pushes an equal volume of drug 30 along the delivery lumen 28, accordingly the pressure inside the vial 26 is promptly equalized to the pressure inside the drip chamber 20.

According to the air-driven vial gates 24, there is no need to introduce any difference between the top portion of the delivery lumen 28 and the top portion of the vent lumen 32. Such embodiments do not even need, in their proper use configuration, a specific location of the vial gate 24 with respect to the drip chamber 20. The vial gate 24 can be either located above the drip chamber 20 or not, since the pressure produced by the air pump 44 can actively push the drug 30 along the delivery lumen 28.

According to some embodiments (e.g. that shown in FIG. 5) the vial gate 24 is directly mounted on the pressure conduit 40. According to some other embodiments (not shown) the vial gate 24 is mounted in a remote position with respect to the pressure conduit 40 and is connected thereto by means of a double tube 50. Any of such different configurations may be advantageously adopted in order to deal with specific issues deriving from the overall arrangement of the dialysis machine 10.

The air-driven vial gates further comprises switch means 54, which are herewith disclosed with specific reference to FIGS. 6.*a* and 6.*b*. Switch means 54 are intended to allow the pressure conduit 40 to alternatively perform two different functions. The first one is the original function for the pressure conduit 40, i.e. to put in air communication the drip chamber 20 and the pressure transducer 38. The second one is a double function: feeding to the vial 26 the air provided by the air pump 44 (function performed by the branch 40') and delivering the drug 30 from the vial 26 to the drip chamber 20 (function performed by the branch 40"). As can be seen in the schematic FIGS. 6.*a* and 6.*b*, the switch means 54 are adapted to alternatively adopt two different configurations. The first configuration (measurement configuration) of the switch means 54, shown in FIG. 6.*a*, ensures the continuity of the pressure conduit and completely cuts off the vial gate 24. In such measurement configuration the switch means 54 allow the pressure conduit 40 to perform its first original function. The second configuration (delivery configuration) of the switch means 54, shown in FIG. 6.*b*, puts in double communication the vial 26 with the pressure conduit 40 allowing the pressure conduit 40 to perform its second double function.

According to the air-driven vial gates 24, the volume of air to be pumped into the vial 26 via the vent lumen 32 is to be determined on the basis of the volume of the drug 30 to be delivered. In general, the volume of air 34 will be larger than the volume of drug 30. As a matter of fact, in determining the air volume, also the inner volume of the delivery lumen 28 should be considered in order to completely empty the lumen. Moreover, also air compressibility should be considered in some cases, e.g. if the vial 26 is placed lower than the drip chamber 20.

Of course during the operation of the air pump 44, the pressure transducer 38 can not provide a meaningful value for the pressure inside the drip chamber. Reliability issues arise for the pressure transducer 38 also when the switch means 54 are in the delivery configuration. Such events can be advantageously dealt with by means of specific settings of the machine 10. For example, since most of the hemodialysis machines are electronically controlled, a specific software setting can be used for dealing with the above and other similar events.

According to some air-driven embodiments of the invention, the air pump 44 can be operated in a manner suitable for adjusting the delivery rate of the drug 30, since the volume of drug 30 which is delivered in a time unit depends on the volume of air which is pumped in the vial in the same time unit. In particular, the delivery rate can be automatically controlled on the base of the pressure measurements provided by the pressure transducer 38. When the pressure transducer 38 is connected to the air buffer 22 of the drip chamber 20 (e.g. when the switch means 54 are in their measurement configuration), the pressure transducer 38 can provide the pressure value inside the air buffer 22. When the pressure transducer 38 is connected to the vial 26 (e.g. when the switch means 54 are in their delivery configuration), the pressure transducer 38 can provide the pressure value inside the vial 26. The instant difference between the two pressure values provides the actual force moving the liquid drug 30 along the delivery lumen 28. According to some air-driven embodiments of the invention, the air-pump 44 is automatically controlled on the base of the pressure difference provided by the pressure transducer 38, so as to adjust the drug delivery rate. In the case of the second type of air-driven embodiments of the invention in which an additional air pump is used, a second pressure transducer measuring the pressure in the pressure conduit connected to the vent lumen 32 may be present. In this particular embodiment the pressure in the pressure conduit connected to the vent lumen and the pressure in the drip chamber may be measured simultaneously and the current pressure difference may be determined at all times.

It is to be noted here that vented spikes are known in the prior art (see for example patent publications US2002/115981 or U.S. Pat. No. 4,396,016) which directly put in fluid communication the interior of a drug container with the outer environment. This known solution is not suitable for operation in a haemodialysis circuit 36, due to the pressure difference between the outer environment and the interior of the haemodialysis circuit 36.

Specifically, upstream the blood pump, underpressure is established in the circuit 36 with respect to atmospheric pressure. Accordingly, upstream the blood pump, a venting fluid communication with outer environment would result in the drip chamber 22 being filled with ambient air immediately after delivery of the drug 30. Conversely, downstream the blood pump, overpressure is established in the circuit 36 with respect to atmospheric pressure. Accordingly, downstream the blood pump, venting by ambient air is not possible at all.

Consequently, the venting lumen 32 connected to a closed gas reservoir, allows carrying out different effective solutions according to the invention. Specifically, as described above, the tubing set 12 according to the inventions allows both gravity-driven solutions, wherein the venting lumen 32 is connected to the air buffer 22 of the drip chamber 20, and air-driven solutions, wherein the venting lumen 32 is connected to an air reservoir in which pressure is controlled by an air pump 44.

Both in the gravity-driven and in the air-driven embodiments, the opening at the top end 48 of the delivery lumen 28 is advantageously placed so as to be, when the vial 26 is properly connected to the vial gate 24, as close as possible to the puncturable membrane 52 of the vial 26. An opening of the delivery lumen which is very close to the membrane 52 allows a very effective emptying of the vial 26, i.e. allows a complete delivery of the drug 30.

The vial gate 24 is intended as a delivery point for several different drugs. Accordingly, when the delivery of a first drug comes to an end, the related first vial 26 can be removed and replaced by a second vial 26 containing a second drug. If incompatibility issues occur between the first and the second drug, one or more of the following expedients can be adopted.

As a first expedient, the delivery lumen 28, intended to successively contain the flows of the two incompatible drugs, may be advantageously designed so as to be as short as possible. In such a way, the remainder droplets of the first drug, which will be mixed with the flow of the second drug, are minimized. This solution can be obtained for example by mounting the vial gate 24 directly on the top wall of the drip chamber 20 (see FIGS. 4 and 9 to 11) or directly on the pressure conduit 40 as close as possible to the drip chamber 20 (see FIG. 5).

As a second expedient, the delivery lumen 28 may advantageously comprise means suitable for minimizing the adhesion of the drug droplets. Such means may in turn comprise an inner layer having low adhesion properties. A lumen with such an inner layer may be manufactured by co-extrusion, polymer grafting or coating with a low adhesion material known in the art. For example one solution is to have a surface obtained from a very hydrophobic material, for example from Poly-TetraFluoroEthylene (PTFE) or of other similar materials. Another solution is to attach a hydrophilic hydrogel by coating or grafting and thereby increasing the fluid flow on the surface by enhancing the wettability. This solution and some related methods for providing a hydrogel coating on a polymer substrate are described for example in U.S. Pat. No. 7,572,489.

As a third expedient, a washing solution, for example a saline solution, may be used for washing the delivery lumen 28 so as to remove the remainder droplets of the first drug before the delivery of the second drug. Such washing solution may be for example supplied by means of a simple vial 26. Otherwise the washing solution may be supplied by the substitution liquid circuit which is available on some machines 10. As a matter of fact, most of the recent hemodialysis machines 10 are designed according to the scheme of FIG. 3 rather than those of FIG. 1 or 2. Such machines 10 are intended to perform also hemofiltration and/or hemodiafiltration treatments. Such treatments imply the removal of some waste water from the blood and, accordingly, they need also to compensate the removal by means of the addition of substitution liquid 60. Thus, hemofiltration machines comprise also a substitution circuit 64. In the latter case, the substitution circuit 64 may advantageously comprise a fake vial 62, fed by the substitution liquid 60 flowing in the circuit 64, and suitable for being connected to the vial gate 24 exactly like a common vial 26.

The delivery of drugs from a lot of vials 26 in quick succession may improperly increase the liquid level inside the drip chamber 20. In such a case, exactly as described above, the service staff or the dialysis machine 10 itself can operate the pump 44 to supply lacking air in the drip chamber 20 and to restore the correct air buffer 22 and blood level.

The air pump 44 may also be activated as a precautionary step of the drug delivery method. A volume of air equal to the volume of drug 30 in the vial 26 may be introduced in the drip chamber 20 prior to the drug delivery. In case of air-driven vial gate 24, attention should be paid to the correct position of the switch means 54. In order to properly introduce air 34 in the drip chamber 20 the switch means 54 have to be in the measurement configuration (FIG. 6.a). Otherwise, if the switch means 54 were in the delivery configuration (FIG. 6.b), the activation of the air pump 44 would result in the prompt delivery of the drug 30. The precautionary air supply avoids any possible improper reduction of the air buffer 22.

The invention also relates to a method for delivering a drug 30 in a hemodialysis extra-corporeal circuit 36. The method comprises the steps of:

providing a machine 10 for carrying out a hemodialysis treatment of a patient's blood;
providing the machine 10 with a tubing set 12 according to the invention;
connecting a vial 26 to the vial gate 24, so as to put in communication the interior of the vial 26 both with a delivery lumen 28 and with a vent lumen 32, the delivery lumen being suitable for delivering the drug 30 to the drip chamber 20, and the vent lumen 32 being suitable for providing air 34 inside the vial 26 in order to replace the delivered drug 30.

According to some general embodiments of the invention, the method further comprises one or more of the following steps:

opening the fluid connection between the vial 26 and the extra-corporeal circuit 36 by means of the safe connection means 56;
adjusting the delivery rate of the drug 30 by means of the adjusting means 58.
operating the air pump 44 so as to feed to the drip chamber 20 a volume of air 34 equal to the volume of drug 30 to be delivered;
setting the switch means 54 in their delivery configuration and, subsequently, operating the air pump 44 so as to feed to the vial 26 a volume of air 34 determined on the basis of the volume of drug 30 to be delivered;
closing the fluid connection between the vial 26 and the extra-corporeal circuit 36 by means of the safe connection means 56 and, subsequently, removing the vial 26 from the vial gate 24.

In view of the above description, the skilled person will easily appreciate that the present invention overcomes most of the drawbacks pointed out with respect to the prior art. In particular, the present invention avoids the double transfer of the drug, from the vial to the syringe first and then from the syringe to the extra-corporeal circuit.

Moreover the present invention avoids the use of some disposable items, i.e. the conventional syringes and the respective needles.

Finally, the present invention allows slow administering of the drugs that require it, without needing the active presence of the service staff to do so.

The person skilled in the art can bring modifications and/or replacements of described element with equivalent elements to the embodiments of the tubing set and of the vial gate according to the invention described above, in order to satisfy specific requirements, without for this reason departing from the scope of the attached claims.

What is claimed is:

1. A tubing set suitable for use in co-operation with a machine for carrying out a hemodialysis treatment of a patient's blood, said tubing set comprising:

an out-tube for supplying the blood from the patient to a filter of said machine;
an in-tube for supplying the blood from the filter back to the patient;
a drip chamber placed along one of said out-tube or in-tube, adapted to let the blood drip through an air buffer; and
a vial gate for the connection of an inverted vial containing a drug to be delivered into the blood,
said vial gate including a delivery lumen, suitable for delivering the drug from the vial to the drip chamber, and a vent lumen, suitable for providing air inside the vial in order to replace the delivered drug,
the vent lumen putting in communication an interior of the vial with the air buffer of the drip chamber, and the delivery lumen putting in communication the interior of the vial with the drip chamber, and
a top end of the vent lumen reaching a higher position inside the vial with respect to a top end of the delivery lumen so as to effect the delivery of the drug from the vial to the drip chamber, with the top end of the vent lumen extending into an air space at a top section of the inverted vial.

2. The tubing set according to claim 1, wherein said air buffer is under a pressure which is different from atmospheric pressure.

3. The tubing set according to claim 1, wherein said vial gate includes a connecting element for ensuring a safe connection of the vial, the connecting element being so arranged that the fluid connection can be opened only when the vial is properly placed on the vial gate and, respectively, the vial can be removed only when the fluid connection is closed.

4. The tubing set according to claim 1, wherein the vial gate includes an adjusting element for adjustably obstructing an inner cross section of the delivery lumen so as to adjust a delivery rate of the drug.

5. The tubing set according to claim 1, wherein the drip chamber is placed along the in-tube.

6. The tubing set according to claim 1, wherein the delivery lumen includes an inner layer having a co-extruded construction, a polymer grafted construction, or a construction of a coating with a low adhesion material, suitable for minimizing adhesion of droplets of the drug.

7. The tubing set according to claim 6, wherein said low adhesion material is a highly hydrophobic material.

8. The tubing set according to claim 6, wherein said low adhesion material is a hydrophilic hydrogel.

9. The tubing set according to claim 1, further comprising a substitution liquid circuit feeding a false vial for washing the delivery lumen so as to remove any remainder droplets of the drug before the delivery of a subsequent drug.

10. The tubing set according to claim 1, wherein an inner diameter of the top end of the delivery lumen is larger than an inner diameter of the top end of the vent lumen.

11. The tubing set according to claim 1, further comprising an air pump and a pressure conduit associated with the drip chamber, with the pressure conduit connecting the air buffer with the air pump.

12. The tubing set according to claim 11, wherein said pressure conduit includes a pressure transducer suitable for measuring the pressure inside at least one of the drip chamber and the vial.

13. A method of delivering a drug in a hemodialysis extra-corporeal circuit, said method comprising the steps of:
providing a machine for carrying out a hemodialysis treatment of a patient's blood;

providing the machine with the tubing set according to claim 1; and connecting the vial containing the drug to the vial gate, so as to put in communication the interior of the vial both with the delivery lumen and with the vent lumen, the delivery lumen being suitable for delivering the drug to the drip chamber, and the vent lumen being suitable for providing air inside the vial in order to replace the delivered drug.

14. The method according to claim 13, further comprising the step of operating an air pump so as to feed to the drip chamber a volume of the air equal to the volume of the drug to be delivered.

15. The method according to claim 13, further comprising the steps of setting a switch in the delivery configuration and, subsequently, operating the air pump so as to feed to the vial a volume of the air determined on a basis of the volume of the drug to be delivered.

16. A tubing set for use in co-operation with a machine for carrying out a hemodialysis treatment of blood of a patient, said tubing set comprising:

an out-tube for supplying the blood from the patient to a filter of the machine;

an in-tube for supplying the blood from the filter back to the patient;

a drip chamber placed along one of the out-tube and the in-tube, adapted to let the blood drip through an air buffer;

a vial gate for the connection of a vial containing a drug to be delivered into the blood, the vial gate including a delivery lumen for delivering the drug from the vial to the drip chamber, and a vent lumen for providing air inside the vial in order to replace the delivered drug, the vent lumen communicating an interior of the vial with the air buffer, and the delivery lumen communicating the interior of the vial with the drip chamber; and a substitution liquid circuit feeding a false vial for washing the delivery lumen so as to remove any remainder droplets of the drug before the delivery of a subsequent drug.

17. The tubing set according to claim 16, wherein the connected vial is in an inverted orientation.

\* \* \* \* \*